United States Patent
Fuentes et al.

(10) Patent No.: US 8,070,482 B2
(45) Date of Patent: Dec. 6, 2011

(54) COMBUSTION CONTROL SYSTEM OF DETECTION AND ANALYSIS OF GAS OR FUEL OIL FLAMES USING OPTICAL DEVICES

(75) Inventors: Oscar Francisco Farias Fuentes, Concepción (CL); Daniel Gerónimo Sbarbaro Hofer, Concepción (CL); Robinson Eugenio Betancourt Astete, Temuco (CL)

(73) Assignees: Universidad de Concepción, Concepcion (CL); Universidad de la Frontera, Temuco (CL); ANWO S.A, La Reina-Santiago (CL)

( * ) Notice: Subject to any disclaimer, the term of this patent is extended or adjusted under 35 U.S.C. 154(b) by 0 days.

(21) Appl. No.: 12/139,657

(22) Filed: Jun. 16, 2008

(65) Prior Publication Data

US 2009/0017406 A1    Jan. 15, 2009

(30) Foreign Application Priority Data

Jun. 14, 2007   (CL) .................................. 1742/2007

(51) Int. Cl.
  *F23N 5/00*   (2006.01)
(52) U.S. Cl. ................ 431/76; 431/12; 431/18; 431/24; 431/79; 73/23.31; 73/23.32; 73/23.35; 236/14; 237/2 A; 237/2 R; 237/7; 237/12
(58) Field of Classification Search .............. 431/12, 431/18, 76, 79, 24; 73/23.2, 23.21, 23.22, 73/23.35, 23.36, 23.38, 31.05, 23.31, 23.32; 236/14; 237/2 A, 2 R, 7, 12
See application file for complete search history.

(56) References Cited

U.S. PATENT DOCUMENTS

| | | | | |
|---|---|---|---|---|
| 2,404,903 A * | 7/1946 | Cohen | | 431/79 |
| 2,592,847 A * | 4/1952 | Babicz | | 431/79 |
| 2,804,131 A * | 8/1957 | Ator | | 431/79 |
| 3,080,708 A * | 3/1963 | Carr | | 60/208 |
| 3,292,855 A * | 12/1966 | Wright | | 431/12 |
| 3,368,753 A * | 2/1968 | Baumgartel et al. | | 236/14 |
| 3,369,749 A * | 2/1968 | Siegmund et al. | | 431/12 |
| 3,374,950 A * | 3/1968 | Menzel et al. | | 431/12 |
| 3,814,570 A * | 6/1974 | Guigues et al. | | 431/76 |

(Continued)

FOREIGN PATENT DOCUMENTS

CA    2165350    2/1997

(Continued)

OTHER PUBLICATIONS

Angulo, J. et al., Segmentación de imágenes en color utilizando histogramas bi-variables en espacios color polares luminancia/saturación/matiz, Revista "Computación y Sistemas", vol. 8, No. 4, Jun. 2005, pp. 1-19. (article including English Abstract—19 pages total), Spanish w/English Abstract.

(Continued)

*Primary Examiner* — Steven B McAllister
*Assistant Examiner* — Daniel E Namay
(74) *Attorney, Agent, or Firm* — Hasse & Nesbitt LLC; Daniel F. Nesbitt (57) ABSTRACT

A system of detection and analysis of gas or fuel oil flames using optical devices, consisting of a sensor that targets the flame's reaction zone through an optical access, a processing and control module, and an actuator, responsible for controlling the damper. The system optimizes combustion equipment operation by controlling the damper, obtaining better performance and reducing polluting emissions.

15 Claims, 6 Drawing Sheets

U.S. PATENT DOCUMENTS

| | | | | |
|---|---|---|---|---|
| 3,861,855 A * | 1/1975 | Seider | | 431/76 |
| 3,902,841 A * | 9/1975 | Horn | | 431/79 |
| 4,039,844 A * | 8/1977 | MacDonald | | 250/554 |
| 4,043,742 A | 8/1977 | Egan et al. | | |
| 4,362,499 A | 12/1982 | Nethery | | |
| 4,435,149 A | 3/1984 | Astheimer | | |
| 4,455,656 A | 6/1984 | Tanaka et al. | | |
| 4,461,615 A | 7/1984 | Inoue | | |
| 4,509,912 A | 4/1985 | VanBerkum | | |
| 4,553,924 A | 11/1985 | Nelson et al. | | |
| 4,653,998 A * | 3/1987 | Sohma et al. | | 431/79 |
| 4,820,046 A * | 4/1989 | Sohma et al. | | 356/328 |
| 4,913,647 A * | 4/1990 | Bonne et al. | | 431/12 |
| 5,112,215 A * | 5/1992 | Frish et al. | | 431/3 |
| 5,139,412 A * | 8/1992 | Kychakoff et al. | | 431/12 |
| 5,186,146 A * | 2/1993 | Sohma et al. | | 123/406.28 |
| 5,222,887 A * | 6/1993 | Zabielski, Sr. | | 431/12 |
| 5,249,954 A * | 10/1993 | Allen et al. | | 431/14 |
| 5,252,060 A * | 10/1993 | McKinnon et al. | | 431/12 |
| 5,257,496 A * | 11/1993 | Brown et al. | | 60/773 |
| 5,263,851 A * | 11/1993 | Hosome et al. | | 431/79 |
| 5,275,553 A * | 1/1994 | Frish et al. | | 431/76 |
| 5,303,684 A * | 4/1994 | Brown et al. | | 123/435 |
| 5,368,471 A * | 11/1994 | Kychakoff et al. | | 431/12 |
| 5,480,298 A * | 1/1996 | Brown | | 431/79 |
| 5,487,266 A * | 1/1996 | Brown | | 60/776 |
| 5,544,478 A * | 8/1996 | Shu et al. | | 60/773 |
| 5,547,369 A * | 8/1996 | Sohma et al. | | 431/75 |
| 5,578,828 A * | 11/1996 | Brown et al. | | 250/342 |
| 5,607,294 A | 3/1997 | Gianpiero et al. | | |
| 5,659,133 A * | 8/1997 | Sims et al. | | 73/114.09 |
| 5,691,700 A * | 11/1997 | Phelps et al. | | 340/600 |
| 5,785,512 A * | 7/1998 | Cormier | | 431/79 |
| 5,794,549 A | 8/1998 | Carter | | |
| 5,971,747 A * | 10/1999 | Lemelson et al. | | 431/12 |
| 5,993,194 A * | 11/1999 | Lemelson et al. | | 431/14 |
| 6,060,719 A * | 5/2000 | DiTucci et al. | | 250/554 |
| 6,071,114 A * | 6/2000 | Cusack et al. | | 431/79 |
| 6,113,384 A * | 9/2000 | Sebastiani | | 431/12 |
| 6,227,842 B1 * | 5/2001 | Lemelson et al. | | 431/12 |
| 6,247,918 B1 * | 6/2001 | Forbes et al. | | 431/12 |
| 6,455,851 B1 * | 9/2002 | Lord et al. | | 250/338.5 |
| 6,468,069 B2 * | 10/2002 | Lemelson et al. | | 431/12 |
| 6,551,094 B2 * | 4/2003 | Fastnacht et al. | | 431/2 |
| 6,780,378 B2 * | 8/2004 | Abbasi et al. | | 422/78 |
| 6,823,662 B1 * | 11/2004 | Yamamoto et al. | | 60/286 |
| 7,217,121 B2 * | 5/2007 | Thomson et al. | | 431/12 |
| 7,280,891 B2 * | 10/2007 | Chase et al. | | 700/275 |
| 7,289,032 B2 * | 10/2007 | Seguin et al. | | 340/578 |
| 7,353,140 B2 * | 4/2008 | Daw et al. | | 702/182 |
| 7,520,744 B2 * | 4/2009 | Wintrich | | 431/122 |
| 7,574,039 B2 * | 8/2009 | Ibrahim et al. | | 382/167 |
| 7,710,280 B2 * | 5/2010 | McLellan | | 340/578 |
| 2004/0033457 A1 * | 2/2004 | Zhang et al. | | 431/79 |
| 2004/0156420 A1 * | 8/2004 | Huston et al. | | 374/121 |
| 2008/0050684 A1 * | 2/2008 | Flynn et al. | | 431/12 |

FOREIGN PATENT DOCUMENTS

| | | | |
|---|---|---|---|
| DE | 4042025 A1 * | 7/1992 | |
| GB | 1 032 697 | 6/1966 | |
| GB | 1 396 384 | 6/1975 | |
| JP | 58035323 A * | 3/1983 | |
| JP | 60-036825 | 2/1985 | |
| JP | 60036824 A * | 2/1985 | |
| JP | 60162121 A * | 8/1985 | |
| JP | 60169015 A * | 9/1985 | |
| JP | 60213725 A * | 10/1985 | |
| JP | 60213727 A * | 10/1985 | |
| JP | 62134418 A * | 6/1987 | |
| JP | 62261819 A * | 11/1987 | |
| JP | 63315829 A * | 12/1988 | |
| JP | 01312319 A * | 12/1989 | |
| JP | 10009562 A * | 1/1998 | |

OTHER PUBLICATIONS

Arias, L. et al., A Measuring Method Based on Photodiodes for the Diagnostic of Optimal Combustion Conditions, printed from Advanced Computational Methods in Heat Transfer X, WIT Transactions on Engineering Sciences, vol. 61, 2008, pp. 201-209. (9 pages).

Boysen, C., Análisis y Control de Llama Mediante Métodos Ópticos, memoria para obtener el titulo de Ingeniero Civil Electrónico, Departamento de Ingenieria Eléctrica, Universidad de Concepción, Chile, 2004, pp. 1-74. (article + 1 page English Abstract—75 pages total), Spanish w/English Abstract.

Farias, O. et al., Diagnóstico de la Combustión de Gas y Petróleo Mediante Análisis del Espectro Visible de la Llama, 8° Congreso Iberoamericano de Ingenieria Mecánica, Cusco (Perú), Oct. 23-25, 2007. (article + 1 page English Abstract—10 pages total), Spanish w/English Abstract.

Farias, O., Diagnostico de al Combustión a Partir del Espectro de Llamas Luminosas, printed from PACAM VI, Six Pan American Congress of Applied Mechanics), Rio de Janeiro, Brazil, Jan. 1999. (article + 1 page English Abstract—5 pages total), Spanish w/English Abstract.

Farias, O., summary and table of contents of "Towards the development of an Optimal Combustion Control in Fuel-Oil Boilers from the Flame Emission Spectrum", Thesis for the Degree of Doctor of Applied Sciences, Laboratory of Thermodynamics, University of Liège, Belgium, Sep. 1997. 3 page Abstract/Summary plus 6 page TOC/Index. (9 pages total).

Khesin, M., Diagnosing and Optimizing Combustion by Frequency Spectra Analysis, Physical Sciences, Inc., Conceptual SpectraTune™ System. (2 pages).

Sbarbaro, D. et al., Real-time monitoring and characterization of flames by principal-component analysis, Combustion and Flame, vol. 132, 2003, pp. 591-595. (5 pages).

Tartari, P. et al., Photodiode for Controlling Combustion (VI), Technical Report for WMTE, University of Liège, Belgium, Mar. 2003. (21 pages).

Vora, P. et al., Linear Models for Digital Cameras, Hewlett-Packard Laboratories, Dept. of Psychology, University of California, Santa Barbara, 2000,pp. 1-6. (6 pages).

Ward Perez-Canto, Monitoreo de Llama en Homo HDT Utilizando Análisis de Imágenes, (memoria para obtener el titulo de Ingeniero Civil Electrónico, Departamento de Ingenieria Eléctrica), Universidad de Concepción, Chile, Jul. 2006. (article + 1 page English abstract—88 pages total) Spanish w/English Abstract, Spanish w/English Abstract.

Zuo B. et al., Pollutant Generation by Combustion of Oil Boilers, Bull. Soc. Chim. Belg., vol. 101, No. 10, 1992. (6 pages).

Flame Doctor® Burner Diagnostic System for Individual Burner Optimization, The Babcock & Wilcox Company, Barberton, Ohio, 2004. (2 pages).

MK Combustion Optimization System, GE Power Systems, Twinsburg, Ohio, GEA-13485. (2 pages).

* cited by examiner

COMBUSTION CONTROL SYSTEM OF DETECTION AND ANALYSIS OF GAS OR FUEL OIL FLAMES USING OPTICAL DEVICES

FIELD OF THE INVENTION

The present invention optimizes gas burner combustion using optical devices to analyze the flame. The optical signals are processed to diagnose the combustion state and optimize burner operations in terms of its efficiency and polluting emissions.

BACKGROUND OF THE INVENTION

Combustion research performed in the Combustion Laboratory has obtained important results based on the use of spectroscopy techniques and CCD imagining techniques. These results, obtained at laboratory level, have characterized different flame types according to the emission of free radicals and shooting particles [see Farias, Combustion Control in a Fuel Oil Boiler Frame the Flame Spectrum (1997) the disclosure of which is incorporated herein by reference.]

Citing Zuo (1992), Tartari & Ngendakumana, [A Photodiode for Combustion Control, (2003) the disclosure of which is incorporated herein by reference.] present the application of photo diodes to detect radicals at particular wavelengths in order to define combustion control variables. This work, made in the laboratory of Thermodynamics of the University of Liége, Belgium in 2002, corresponds to one of the first investigations in the application of photo diodes to sense the photons of specific radicals. The used device corresponds to the combination photo diode-amplifying JIC 1EI17, which can be used externally with fixed or adjustable gain. The photo diode is sensitive in the 210-380 rank nm (UV) and has been used without interference filters. Due to the produced optical phenomena and the lack of rigor in the construction of the electronics responsible for device handling, the results were unsatisfactory.

On the other hand, it has been determined that CCD cameras have a linear spectral response and that this answer depends on the spectral sensitivity of the different sensors or filters for the colors of each camera individually. Additionally, they linearly depend on the incident power density and the wavelength. Finally, the spectral response is affected by noise, which can be diminished with a correct calibration. [Vora, Farell, Tietz and Brainard, (2000)].

Studies of the different color models and the advantages or disadvantages in their use of in different applications exist. The best known color system is the RGB because a computer program can easily decompose an image into the 3 channels of red, green, and blue. Furthermore, these channels are correlated to each other and certain procedures that require independence of the different color channels cannot be performed [Angulo, (2005)].

The HSB (Tonality, Saturation and Brightness) color model does allow this interdependence between the channels and it is very useful for procedures to recognize patterns in images. Additionally, the L*a*b* color model, which also allows us to obtain dependency between the channels, has also been studied [Ward, (2006)].

Several image processing strategies to identify certain indices characteristic of the flames have been developed, making control possible. Furthermore, certain correlations are determined between the luminous signal intensity captured with CCD cameras through their R, G and B filters, and some burner combustion or adjustment parameters. It is concluded that the excess of air in the combustion is correlated with the luminous signal intensity, explaining why these strategies can be used in combustion control. [Boysen, (2004)]

There are two commercial products, Spectra Tune and Flame Doctor, oriented to combustion optimization using optical signals.

SpectraTune is a combustion diagnosis and optimization system based on the analysis of spectral frequency, the visible phantom and the near TO GO, developed by Mark J. Khesin through the company Physical Sciences Inc. At present, the system is commercialized by GE Power Systems under the denomination "MK Optimization Combustion System". Its design is limited to applications in power stations that use pulverized coal and its application depends on operator criteria and does not allow total automatization for burner control. Its cost is around US$ 25,000 for each Burner.

Flame Doctor is a system that provides real time analysis for each burner of a furnace. It analyzes the individual burner performance, identifying those with low yield and provides a diagnosis that orients the necessary adjustments. Flame Doctor uses signals from optical flame sensors, which with mathematical professing tools determine the degree of deviation with respect to the optimal degree. Its application has been developed for coal combustion and its price is in the order of US$ 150,000. The mentioned technologies are oriented to large-size facilities (on 350 MW).

Patent GB1396384 describes a sensor and a furnace control method that uses photoelectric sensors with two attachment lines to intercept the flame, producing two electrical exits or signals (x and y). The system consists of two tubes similar to a telescope, where the photodetector provides the optical image. Two types of sensors can be used: photovoltaic sensors if the fuel is coal or oil and infrared photodetectors if the fuel is natural gas. The signals x and y are processed electronically using a band pass filter of 200 Hz to 1000 hz, post-amplified, rectified and finally the signal is smoothed in a new filter. The time required is between 0 and 5 seconds, and action on the fuel source is soon taken when the flame is not detected.

The system correlates the information in three levels: the first one indicates flame absence, the second one indicates a normal flame, and the last level indicates an intermediate level of abnormal flame. The simple use of these optical radiation detectors (infrared, visible or ultraviolet) is believed to give a false indication about to the flame presence because they receive additional radiation from the furnace walls and a neighboring flame. In a large furnace, there are many burners and it is difficult to have a line of view of only one radiation, considering especially that the flame morphology depends on the fuel source as well as other factors. For these reasons, although devices sensitive to radiation amplitude can work satisfactorily with a single burner, the high level of background radiation disables the use of such devices in a furnace with multiple burners.

This circuit can not only distinguish the flame type, it can also be used to obtain the air-fuel relation, which depends on the flame position and is also influenced by the provided air flow. Therefore, this correlation can be used to obtain a warning device or a control system if the obtained correlation is outside certain range values.

This publication's detectors use the particular characteristics of the flames. One detector is a differentiated system in which two photoelectric cells are placed to observe the dark and light flame areas, respectively. Such a detector is applicable to coal flames where there is a dark area associated to the pulverized coal. Nevertheless, such a detector is very sensitive to changes in combustion conditions that modify the distance along the flame axis in which the fuel ignites. With a differentiated flame detector, the blockage of one of the vision tubes could even cause a differentiated signal when the flame is absent.

This patent publication uses photoelectric sensors to detect the flame presence and thus to act on the fuel source (three levels: without flame, normal flame and intermediate or abnormal flame) in order to provide flame monitoring when there is more than one burner, avoiding fuel injection when the flame has been extinguished in order to avoid possible explosions.

U.S. Pat. No. 4,435,149 describes a sensor and flame control method in a furnace, which manipulates the air/fuel variable in order to maintain maximum furnace efficiency. This sensor is based in the use of a radiometer with an infrared detector to observe the flame. The control system is based on the radiation signals emitted at three different wavelengths, using suitable filters.

The control parameter uses the ratio of at least two signals of infrared radiation to control the fuel/air mixture, maintaining furnace operation at its maximum efficiency. This publication uses a radiometer to detect the intensity emission in the flame's infrared range. The use of the radiometer in the visible spectral radiation range could increase the costs.

British patent GB1032697 publication describes a device for safety control of the flame in gas burners equipped with a pilot flame to ignite the main flame. This control device includes two flame detectors (one normally near to the flame pilot and another one near to the region of the main flame) and the circuit controls the main gas valve, whereas both detectors respond to the flame presence.

There are many flame detectors for this type of application, such as thermocouples, photoelectric cells, elements that respond to flame or gas conductivity and photodiodes in the ultraviolet or infrared range. Therefore, this device is used to maintain a safe flame operation.

U.S. Pat. No. 4,455,656, also discloses a combustion control circuit that includes the integrated circuits of a semiconductor used to control the furnace to warm up water, air or similar. This is a conventional combustion control circuit that uses the temperature signal, which means that the operation exit signal is adjusted using the voltage provided from the source to initialize the circuits.

U.S. Pat. No. 4,461,615, discloses a combustion control device based on the oxygen content, using an electrode in contact with the flame. Depending on the oxygen content and the source's voltage, the detection circuit produces a voltage that is compared with a reference voltage, and this information is used to control the fuel source's valve. The detection system is an intrusive method and the control is applied on the fuel flux. Thus, the control strategy does not consider combustion quality, which in addition to the power control (depending on the fuel flow) is given by air adjustment.

U.S. Pat. Nos. 4,553,924 and 4,509,912 disclose a system that uses an axis union to control the combustion in a furnace in order to maintain an optimal air/fuel mixture relation for all furnace power levels. The system consists of an adjustment of the mechanical connection in which a main arm is connected with an axis to control fuel valves and an auxiliary arm is connected to the air ventilator. This mechanical adjustment establishes a master-slave relation between the fuel and air valves.

U.S. Pat. No. 4,362,499 discloses a combustion control system for a furnace based on the monitoring of content of oxygen and carbon monoxide contents as well as the smoke's temperature in the combustion chamber. This system uses a conventional combustion control circuit based on gas concentration. The measurement parameters are used to calculate the on-line heat loss associated to combustion products. Based on the heat losses, the combustion air is controlled, minimizing heat losses and maximizing the furnace's thermal efficiency under different operation conditions. The disclosed system basically corresponds to a system of conventional combustion control based on the gas concentration and temperature, which corresponds to an invasive method.

Japanese Publication JP60036825 describes a combustion control system based on measuring temperature distributions in a flame without contact. The spectral analysis carried out by a light detector, and then the vibration spectrum of the OH radical is calculated to determine the flame's temperature distribution. This temperature is compared with an optimal distribution stored in the system, and this difference is then used to control the system. Only the radiation of the OH radical is used to determine the temperature distribution and the control action is based on this estimated temperature. The analyzed request is quite different to the proposed method, and thus does not affect this novelty.

U.S. Pat. No. 4,043,742 describes a combustion control system that uses radiation intensity at different, non-specified wavelengths. This ratio is then used by a master controller to regulate the air-fuel ratio. The detector is a complex system consisting of several mechanical and electro-optical components. The detector's signals are used to calculate a ratio between the intensities of two wavelengths that are correlated with the air-fuel ratio.

U.S. Pat. No. 5,971,747 describes a system using several detection techniques, such as CCD cameras, photo detectors, and laser based systems. A neural network analyzes the images and characterizes the combustion flame. Other forms of sensors monitor and generate data signals defining selected parameters of the combustion process. All the signals are analyzed using a fuzzy-logic based system, which generates control signals defining adjustments to optimize the combustion process. This system has many measuring sub-systems requiring sophisticated data processing techniques, resulting in a very complex and expensive system. As a result, this solution is not attractive for small-scale combustion systems.

U.S. Pat. No. 5,794,549 describes a system based on the flame temperature measurement using solid state CCTV cameras in furnaces that operate with pulverized coal. This system involves an image processor, a monitor adapted to exhibit the processed information, and a controller that regulates air-fuel ratio. Its strategy is based on reaching the ideal furnace functioning by controlling NOx emissions since a linear relation exists between the above mentioned emission and the combustion temperature. Coal presents higher NOx emissions that are more temperature dependent than gas and oil. Therefore, this strategy used would not be valid for gas and oil flames U.S. Pat. No. 5,263,851 discloses a control system used in a radiant pipe gas burner installed in an oven. This system is based on the integrated, rectified signal of the voltage given by a germanium photodetector that feeds from the flame's luminous signal transmitted across an optical fiber. The sign of the integrated voltage is related to the fluctuation of the flame's intensity. The control action in this system is exercised in a discrete range to identify incomplete combustion, finished combustion and flame absence conditions. This control system establishes a wide operation region (finished combustion) and does not allow identification of the ideal one.

SUMMARY OF THE INVENTION

The present invention seeks to optimize combustion inside a furnace's home by analyzing the gas flame using optical devices. The optical signals are processed using software that diagnoses the combustion quality and optimizes equipment operation in terms of yield and polluting emissions.

The present invention encompasses a detection and analysis system for gas and oil flames based on optical devices (photo detectors or cameras) and algorithms to diagnose combustion quality and to optimize operation in terms of performance and pollutant emissions.

The present invention relates to a system of detection and analysis of a gas or fuel oil flame using optical devices, including an optical sensor targeting the reaction zone of the flame with an optical access capable of generating a signal; a processing and control module for receiving and processing the signal; and an actuator responsible for damper control, for manipulating the airflow in response to the processed signal.

The present invention also relates to a method of detecting and analyzing a gas or fuel oil flame comprising the steps of:

a) providing a detection and analysis system according to the detection and analysis system described above;

b) generating an optical signal using an optical sensor using an optical access targeted towards the flame's reaction zone;

c) sending the optical signal to the processing and control modules that includes a processing software that generates a control order and an indicator that allows the post-processing software to send the control order to the actuator, and d) regulating the input combustion air with the control order to obtain an ideal burner damper position.

The proposed approach has two differentiating characteristics:

a) The detector devices are simple photodiodes with interference filters for detecting the CH and C2 radicals, clearly establishing the optimum combustion condition.

b) The use of CCD cameras to visualize the reaction zone combined with the use of multivariable histograms obtained from the flames' images and suitable thresholds provide an alternative method for detecting the underperforming combustion states.

The proposed system seeks to satisfy the objectives of optimizing the combustion process using simpler data processing techniques. Its image processing is based on multivariable histograms of the reaction zone. This analysis is used to find the air-fuel ratio that optimizes combustion process efficiency.

DETAILED DESCRIPTION OF THE INVENTION

The invention consists of a system for flame detection and analysis typically of gas and fuel oil, using optical devices, typically photo detectors or cameras, located in the rear part of a furnace or in locations where they can target the flame reaction zone. The optical signals are transmitted to processing and control module, typically a computer system, that uses specific algorithms to process the optical signals, generating indicators to diagnose the combustion quality and to optimize equipment operation in terms of its efficiency and polluting emissions.

This flame detection and analysis system can be used as an autonomous system to diagnose industrial equipment or as part of a combustion control system in existing burners, boilers or industrial furnaces. In the second option, air control can be decoupled from the fuel control system, which is novel compared to traditional control schemes. For this reason, the system includes a control strategy that interacts with typical control equipment, optimizing the use of combustion air.

The invention has the following main components:
a) A sensor (photo detectors or cameras) that it is targeted by an optical path towards the flame reaction zone;
b) A processing and control module;
c) An actuator, to manipulate the air flow.

The system constantly seeks to maintain the equipment operating at maximum, and preferably ideal, performance with the lowest levels of pollutant emissions.

The photo detectors (photodiodes or radiometer) use the spectral information from the flames to generate a control index for optimizing the combustion process. Using emissions of the free radicals CH and C2, centered at 432 and 516 nm respectively, a control strategy based on the ratio between the C2/CH can be established. This parameter is a good indicator of combustion quality since it can detect the conditions under which the burner operates with low pollutant emission levels (CO and soot) yet at high performance. In the case of oil, the spectral information will correspond to soot emissions in wave lengths between 400 and 750 nm.

The sensors (CCD camera or photodiode) must be placed focusing towards the flame's reaction zone, sending the optical signals to a processing unit to be processed. The processing unit generates a combustion state index that is used to identify the best operational conditions and then acts on the actuator, which in turn acts on the servomotor to regulate the combustion air. The silicon photodiodes of the present invention use filters that restrict the intensities received from the flame to narrow bands relative to radical C2 and CH emission. This strategy implies the use of at least 2 photodiodes.

The invention contemplates software for real-time analysis of flames using CCD cameras. A set of images are averaged and then processed according to a predefined method ("clustering", "inter-class", "metric", "entropy", "moments" or manually). This process is performed in different color spaces (RGB, HSV, HSL, HSI), where a number of pixels of 2D Histograms, corresponding to regions of the flame correlated with the formation of pollutant species (CO, soot and NOx), is calculated. This estimated value is used as an index to control the combustion process.

Summarizing, the present invention encompasses a detection and analysis system for gas and oil flames based on optical devices (photo detectors or cameras) and algorithms to diagnose combustion quality and to optimize operation in terms of performance and pollutant emissions.

The developed system achieves reductions in fuel consumption and emissions. Additionally, it has the following advantages compared with conventional systems:

On-line monitoring and control. Traditional systems do not have direct control over the combustion air. As a result, in practice, systems require sporadic regulation by specialized personnel.

In traditional systems, oxygen and carbon monoxide are monitored independently and no connection to define optimal operation is established between these two variables. The developed system synthesizes in a single index combustion criteria required to optimize performance and to control unburned products.

The proposed system provides faster monitoring and control responses. The system monitors the combustion process at its origin, i.e. "the flame's reaction zone", differing from systems based on gas analysis, whose monitors are normally located in the chimney.

Optical sensors are not intrusive. Indeed, measuring flame characteristics by optical methods does not alter boiler or furnace functioning in any way. Thus, system maintenance costs are lower than control systems using a gas analyzer that must be regularly recalibrated due to depositions of soot particles in the measurement probe.

The maintenance cost is low since the devices are easily available in the market. Additionally, their useful life can be from several months to years, depending on the operating conditions, and they can be easily replaced in case of failure.

The proposed system can be configured as either a flame monitoring system or a as a backup control system in the case of main control system failure.

For the users, the system provides the followings economic benefits: fuel savings, operational costs savings, and lower risk of sanctions due to polluting emissions. The system can also provide additional safety and support to an already existing control system.

Example of the Application

The technology has been implemented in a boiler of 150 kW.

In all the cases considered of burner power, it was observed that if the CO emission increases, the control variable C2/CH reaches a maximum value. This result is a clear indication that, in the case of the studied system, the relative presence of radicals does not depend on the power. Therefore, it is possible to work with very low emissions and high performances under different power conditions.

Three strategies of control have been tested:
1. Slope based
2. Gradient Method.
3. Quadratic algorithm for extreme searching.

Figure 1:
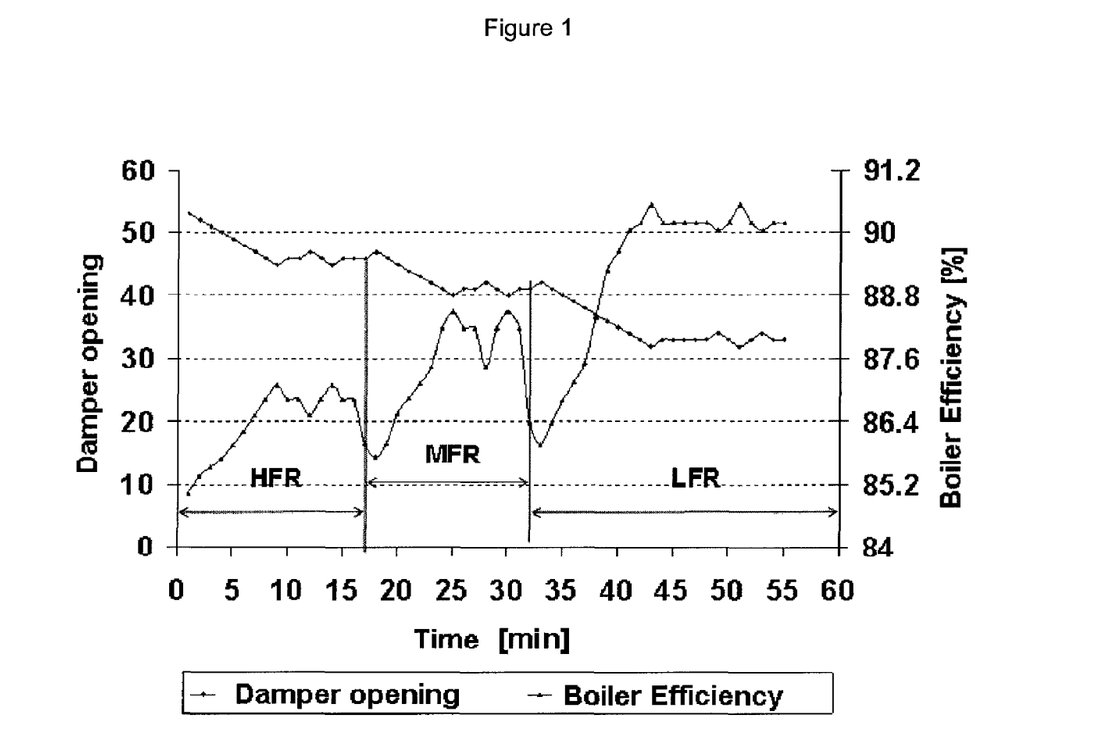
FIG. 1 shows results of the implementation of the flame detection and analysis system in a boiler, showing specifically damper opening and boiler efficiency, versus time.
Figure 2:
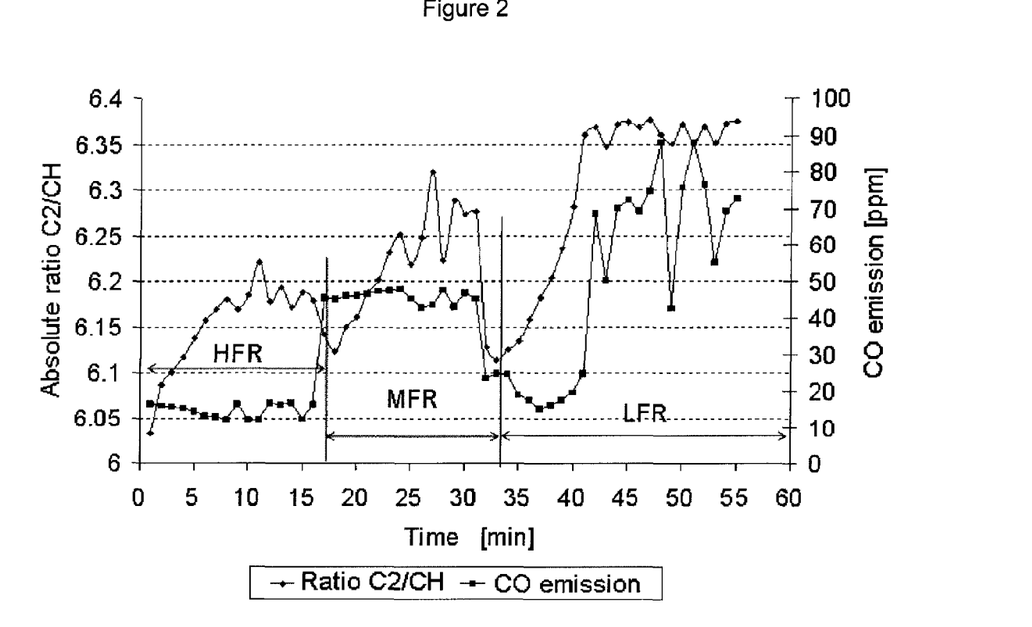
FIG. 2 shows the results of the operation described in FIG. 1, showing specifically the ratio C2/CH and the CO emissions, versus time.

The search strategy for the slope value is based on a simple comparison algorithm, which determines the slope between the ratio C2/CH and the damper opening in order to compare it to the desired slope. Since in this case, the slope is zero at the point of maximum operation, the control strategy changes burner power. The results obtained using this method are depicted in FIGS. 1 and 2. This method takes nearly 10 minutes to find the optimal point of burner operation. The boiler efficiency obtained is 86% and the CO emission is under the 100 ppm. In FIG. 1, the line with rhombuses corresponds to damper opening and the line with triangles corresponds to boiler efficiency. In FIG. 2, the line with rhombuses corresponds to the ratio C2/CH and the line with squares corresponds to CO emissions.

Figure 3:
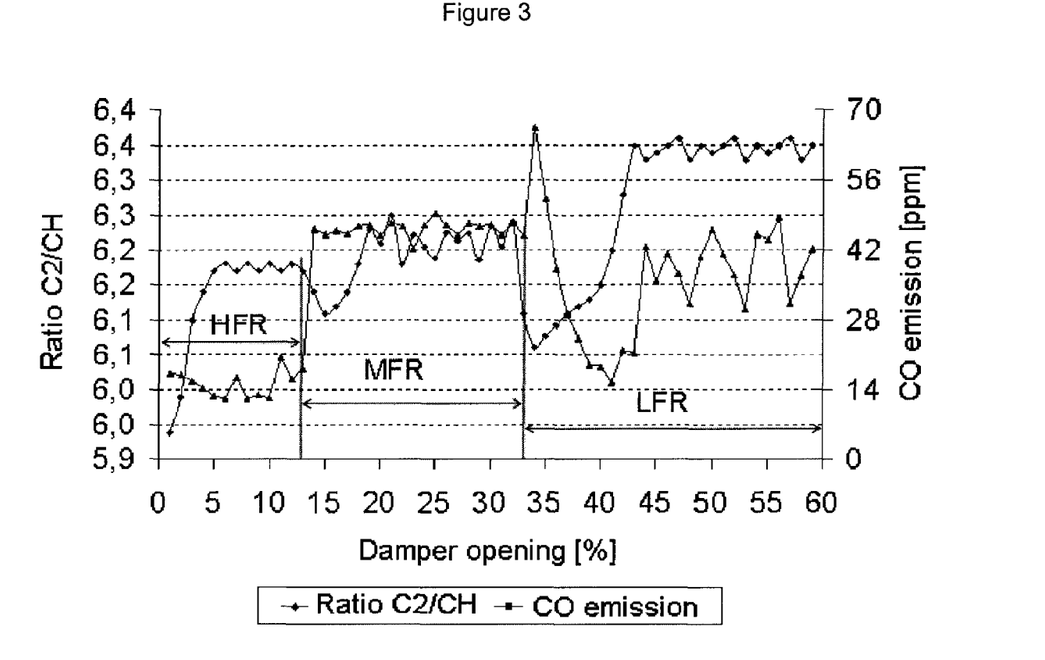
FIG. 3 shows an operation where C2/CH is maximized, showing specifically the ratio C2/CH and the CO emissions, versus time.
Figure 4:
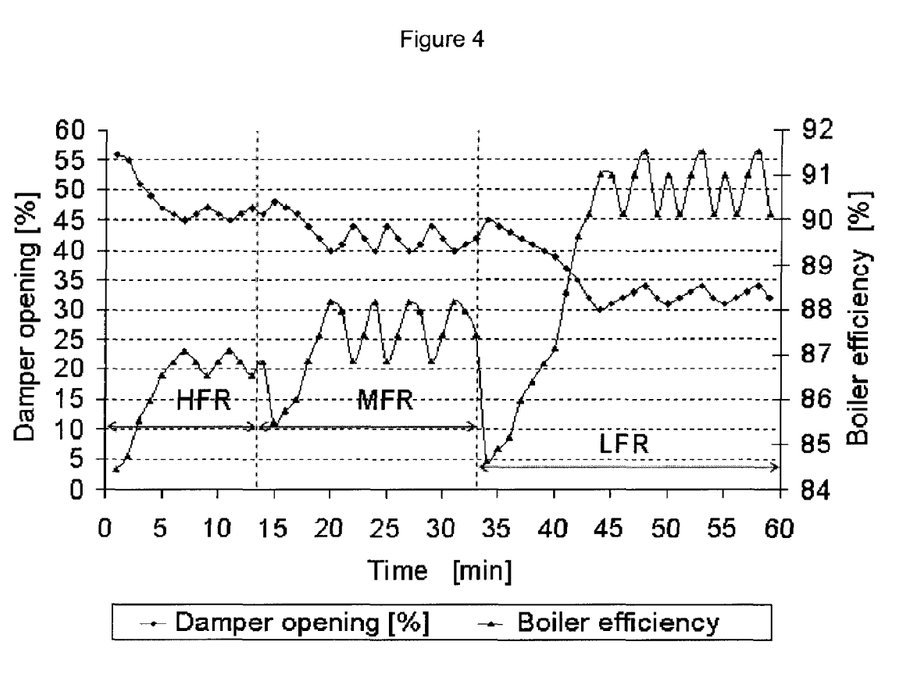
FIG. 4 shows the results of the operation described in FIG. 3, showing specifically the damper opening and the boiler efficiency, versus time.

The gradient method is based on the equilibrium condition, where the method determines to open or close the damper in order to obtain the position where ratio C2/CH is maximized. This method needs to know the gradient between the ratio C2/CH and the damper opening. FIGS. 3 and 4 show the results obtained using this method, where the boiler efficiency is over 84% and the CO emissions under the 100 ppm.

The quadratic algorithm method fits the curves obtained from the ratio C2/CH for different burner power levels to a Taylor series (Equation 1), discarding the terms larger than the third order. Thus, it is possible to obtain the damper opening that maximizes the ratio C2/CH.

$$R_k = \sum_{i=0}^{\infty} \frac{1}{i!} \frac{\partial^i}{\partial x^i} F(x^*) \cdot (x_k - x^*)^i \qquad (1)$$

Figure 5:
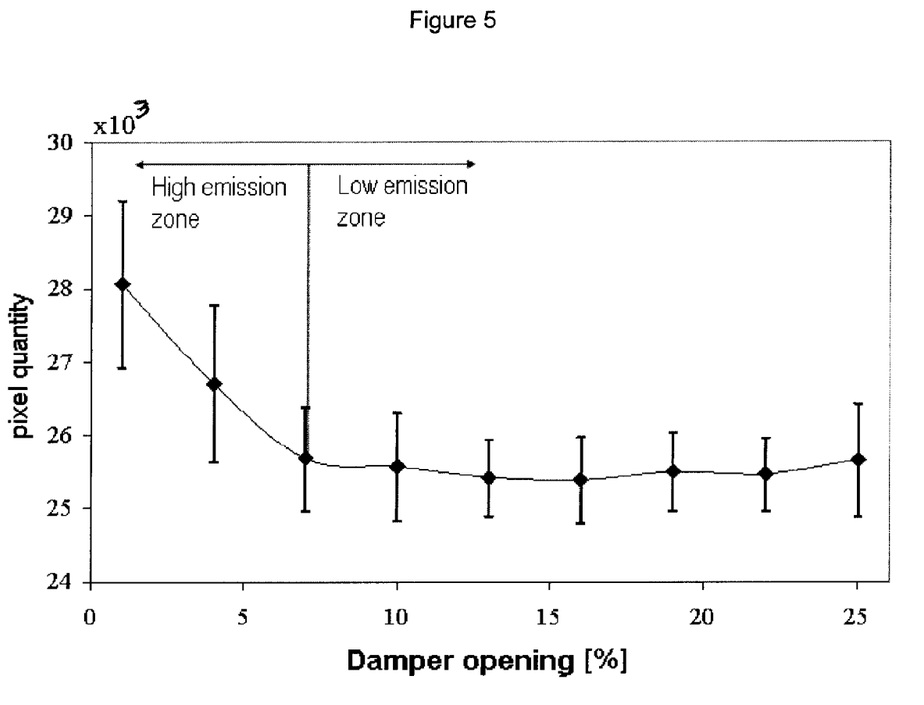
FIG. 5 shows the application of the control strategy with a CCD camera, showing the image index as number of pixels, and the damper opening.

FIG. 5 shows the application of the control strategy, using a CCD camera installed in the boiler for an operation with natural gas. In FIG. 5, it can be observed how the image index, obtained by post-processing software, is able to follow the changes in the regulation variable that corresponds to the opening of the air input valve. Indeed, it can be especially observed that the increased signal corresponds to a condition when the combustion deteriorates. The system then marks the guideline to control the equipment to reach an ideal point in order to obtain maximum boiler efficiency with CO emissions at acceptable levels according to international standards.

Figure 6:
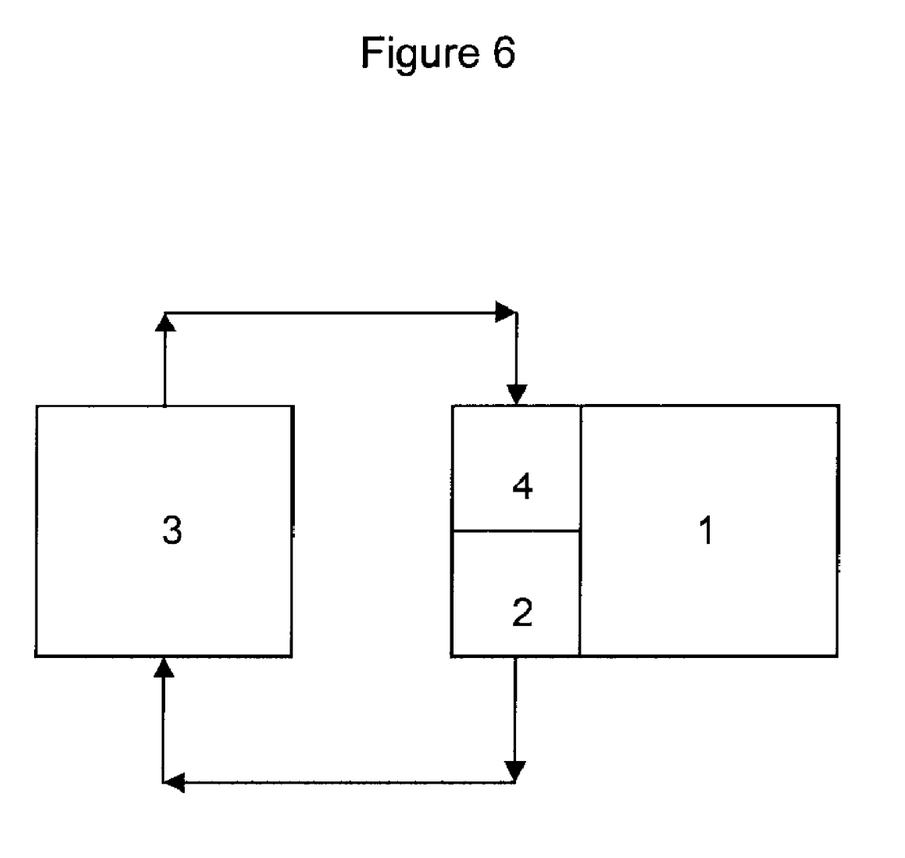
FIG. 6 depicts the general control scheme of a boiler's burner.

Summarizing, FIG. 6 depicts the general control scheme implemented in a boiler's burner. We can see: the combustion chamber where the flame lodges (1), the sensor (2) that records the selected signals emitted by the flame, the processing and control module (3) and the actuator (4) that acts on the burner damper.

What is claimed is:

1. A system of detection, analysis, and control of a gas or fuel oil flame of a burner of a boiler, industrial furnace or other equipment with a combustion process, including:
   a. an optical sensor that targets the reaction zone of the flame, including a first photodetector for detecting an emission of the gas or fuel oil flame at 432 nm and generating a first signal as the absolute intensity of free radical CH, and a second photodetector for detecting the emission of the flame at 516 nm and generating a second signal as the absolute intensity of free radical C2;
   b. a processing and control module receiving and processing the first signal and second signal, and generating a processed signal corresponding to a ratio of the second signal to the first signal; and
   c. an actuator receiving the processed signal as an input and manipulating and controlling an airflow damper in response to the processed signal wherein the processing and control module constantly monitors the CH and C2 levels and constantly sends a signal to the actuator to adopt an ideal burner damper position by constantly maximizing the ratio of C2/CH, thereby increasing boiler efficiency and diminishing pollutant emission levels.

2. The system according to claim 1, where the optical sensor is located in a rear part of the burner.

3. The system according to claim 1, wherein the combustion air control system is disconnected from the fuel control system.

4. The system according to claim 1, wherein the spectral information of the flame generates a control index that is used to optimize the quantity of combustion air entering into the burner.

5. The system of according to claim 1, further including a third photodetector for detecting in wave lengths between 400 nm and 750 nm, as a measure of soot emission, for controlling the fuel oil.

6. The system according to claim 1, wherein the sensor is selected from the group consisting of a CCD camera and a photodiode.

7. A method of detecting and analyzing a gas or fuel oil flame in a boiler or other equipment with combustion processes, in order to increase boiler efficiency and diminish pollutant emission levels, comprising the steps of:
   a) providing the detection, analysis, and control system according to claim 1;
   b) generating an optical signal using an optical sensor with an optical access targeted towards the flame's reaction zone, the optical signal including a first signal as the absolute intensity of free radial CH detected at 432 nm, and a second signal as the absolute intensity of free radial C2 detected at 516 nm;
   c) sending the optical signal to the processing and control modules that includes a processing software, that generates a control order consisting of a processed signal based on a ratio of the second signal to the first signal, and an indicator that allows the post-processing software to send the control order to the actuator; and
   d) regulating the input combustion air with the control order to obtain an ideal burner damper position,
   wherein the processing and control module constantly searches and adopts an ideal burner damper position where the ratio of C2/CH is maximized, thereby increasing boiler efficiency and diminishing pollutant emission levels.

8. The method according the claim 7 wherein the processing software analyzes the optical signal of the flame in real time.

9. The method according to claim 8 wherein the processing software defines a threshold for an average image in agreement with a predefined method, where the predefined method is selected from the group consisting of clustering, inter-class, metric, entropy, moments and manually.

10. The method according to claim 9 further comprising filtering image in the different color spaces, and defining the indexes to characterize the combustion state.

11. The method according to claim 9, further comprising calculating the number of pixels in different 2D histograms, associating them to the color spaces that are representative of the flame regions and that denote pollutant species formation, and sending a calculated value as a control index to a screen or in a text file.

12. The method according to claim 7 wherein the processing software defines a threshold for an average image in agreement with a predefined value, where the predefined value is determined by a method selected from the group consisting of a slope-based method, a gradient-based method, and a quadratic algorithm for extreme searching-based method.

13. The system according to claim 1 wherein the optical sensor is located in the rear part of the boiler or furnace.

14. The system according to claim 1 wherein fuel flow rate is held constant.

15. The method according to claim 7 further comprising the step of holding constant the fuel flow rate in the provided detection, analysis, and control system.

* * * * *